(12) United States Patent
Hunter et al.

(10) Patent No.: US 7,550,031 B2
(45) Date of Patent: Jun. 23, 2009

(54) CYLINDER FILLING OXYGEN CONCENTRATOR

(75) Inventors: Donald W. Hunter, Somerset, PA (US); Frank R. Frola, Somerset, PA (US); Karl Bowser, Friedens, PA (US)

(73) Assignee: Sunrise Medical HHG Inc., Longmont, CO (US)

( * ) Notice: Subject to any disclaimer, the term of this patent is extended or adjusted under 35 U.S.C. 154(b) by 344 days.

(21) Appl. No.: 11/550,442

(22) Filed: Oct. 18, 2006

(65) Prior Publication Data

US 2007/0084342 A1    Apr. 19, 2007

Related U.S. Application Data

(60) Provisional application No. 60/728,595, filed on Oct. 19, 2005.

(51) Int. Cl.
B01D 53/02 (2006.01)
F04B 23/04 (2006.01)
F04B 23/08 (2006.01)

(52) U.S. Cl. .......................... 95/130; 95/121; 96/127; 96/128; 96/130; 128/204.18; 417/62; 417/199.1

(58) Field of Classification Search .................. 95/121, 95/130; 96/127–128, 130; 128/204.18–206.19; 417/62, 199.1
See application file for complete search history.

(56) References Cited

U.S. PATENT DOCUMENTS

| | | | |
|---|---|---|---|
| 4,552,571 A | 11/1985 | Dechene | |
| 4,636,226 A | 1/1987 | Canfora | |
| 4,673,415 A | 6/1987 | Stanford | |
| 5,071,453 A | 12/1991 | Hradek et al. | |
| 5,163,978 A | 11/1992 | Leavitt et al. | |
| 5,354,361 A | 10/1994 | Coffield | |
| 5,368,019 A | 11/1994 | Latorraca | |
| 5,858,062 A * | 1/1999 | McCulloh et al. | 95/8 |
| 5,988,165 A | 11/1999 | Richey, II et al. | |
| 6,302,107 B1 | 10/2001 | Richey, II et al. | |
| 6,394,089 B1 | 5/2002 | Cantrill et al. | |
| 6,446,630 B1 | 9/2002 | Todd, Jr. | |
| 6,660,065 B2 | 12/2003 | Byrd et al. | |
| 6,712,877 B2 | 3/2004 | Cao et al. | |
| 6,805,122 B2 | 10/2004 | Richey, II et al. | |
| 6,889,726 B2 | 5/2005 | Richey, II et al. | |
| 6,904,913 B2 | 6/2005 | Aylsworth et al. | |
| 2005/0103341 A1 | 5/2005 | Deane et al. | |

* cited by examiner

*Primary Examiner*—Duane Smith
*Assistant Examiner*—Anthony Shumate
(74) *Attorney, Agent, or Firm*—MacMillan, Sobanski & Todd, LLC

(57) ABSTRACT

An energy efficient oxygen concentrator for filling high pressure portable cylinders with medical oxygen for use by ambulatory patients. Two compressors provide two pressurized air sources, one for operating an oxygen concentrator to provide a stream of oxygen enriched gas, and the other for driving a pressure intensifier for filling portable oxygen cylinders. Pressurized exhaust from the pressure intensifier is returned to the inlet side of at least one of the compressors for reducing the energy required to drive the compressor. Preferably, each compressor has a single reciprocating piston, a single motor drives both pistons and the pressurized exhaust from pressure intensifier is provided to the inlets for both compressors.

10 Claims, 1 Drawing Sheet

CYLINDER FILLING OXYGEN CONCENTRATOR

CROSS-REFERENCE TO RELATED APPLICATIONS

Applicants claim priority to U.S. Provisional Patent Application Ser. No. 60/728,595 filed Oct. 19, 2005.

STATEMENT REGARDING FEDERALLY SPONSORED RESEARCH OR DEVELOPMENT

Not Applicable.

TECHNICAL FIELD

The invention relates to a medical oxygen concentrator combined with a pressure intensifier for filling a portable oxygen cylinder for use primarily by ambulatory persons.

BACKGROUND OF THE INVENTION

Medical oxygen is normally provided to patients who require supplemental oxygen either from pressurized cylinders delivered to the patient's home or from an oxygen concentrator. An oxygen concentrator separates nitrogen from air to provide an oxygen enriched gas having a concentration of up to about 95% oxygen. The oxygen concentrator operates by using a compressor to apply pressurized air to a gas separation element, such as a molecular sieve bed, which will pass oxygen while having an affinity for nitrogen. Over a relatively short time, the gas separation element will become saturated with nitrogen and its efficiency decreases. Typically, an oxygen concentrator is provided with two or more molecular sieve beds. While at least one molecular sieve bed is operated to produce a flow of oxygen enriched gas, nitrogen is purged from at least one other molecular sieve beds by a limited back flow of the nitrogen free oxygen enriched gas from an operating sieve bed.

A common type of compressor used to operate an oxygen concentrator comprises a single electric motor having two reciprocating piston compressors driven from opposite ends of the motor shaft. Each compressor includes a piston which is reciprocated in a cylinder by the motor. The two cylinders are connected together to provide the air flow and pressure required to produce a desired maximum oxygen enriched gas output. An oxygen concentrator may be designed, for example, to provide a maximum continuous flow of 5 liters per minute, or more, of oxygen enriched gas having an oxygen concentration of up to about 95% at a pressure of 8.5 psig.

Oxygen enriched gas from an oxygen concentrator is delivered to the patient through a hose and a nasal cannula. The hose may be sufficiently long to allow the patient to walk around an area of his or her home. However, most oxygen concentrators are not sufficiently small and light weight to allow an ambulatory patient to leave the home. For trips away from the home, either a portable compressed oxygen cylinder or a portable liquid oxygen container are typically used to provide the patient's supplemental oxygen needs. Oxygen dealers deliver filled portable oxygen cylinders to the patient's home as needed by an ambulatory patient when traveling away from the home oxygen source. Regular home delivery of oxygen results on an ongoing high expense either for insurance companies or for the patient.

In addition to supplying oxygen enriched gas directly to a patient, some oxygen concentrators have been connected to a compressors or to a pressure intensifiers for increasing the gas pressure of the oxygen enriched gas product stream to the level needed for filling a portable cylinder which the patient may use when traveling away from the home. When the oxygen concentrator simultaneously provides the patient's requirements for supplemental oxygen and fills a cylinder, the time required to fill the cylinder is long, since the patient's needs must be met first and only oxygen enriched gas in excess of the patient's needs can be used to fill the cylinder. In some prior art cylinder filling oxygen concentrators, a separate stand alone motor driven compressor is used to increase the gas pressure to the level needed to fill the cylinder. In other cylinder filling oxygen concentrators, a portion of the above atmospheric pressure oxygen enriched gas from the oxygen concentrator has been used to drive a pressure intensifier which increases the pressure to the high level required to fill the cylinder.

BRIEF SUMMARY OF THE INVENTION

According to the invention, apparatus is provided for producing oxygen enriched gas and for filling portable high pressure oxygen cylinders with the gas. Two reciprocating piston compressors are provided, one for supplying a flow of pressurized air to operate the oxygen concentrator and one for providing a flow of pressurized air for driving a pressure intensifier. The above atmospheric pressure exhaust air from the pressure intensifier is returned to the inlet of at least one of the compressors, and preferably to the inlets of both compressors, to increase the efficiency of the oxygen concentrator. Preferably, the reciprocation pistons of the two compressors are driven from opposite ends of a motor shaft. One compressor cylinder is connected to provide pressurized feed air to an oxygen concentrator. The other cylinder is connected to provide pressurized air for driving a pressure intensifier which increases the pressure of the oxygen enriched gas stream from the oxygen concentrator. Above atmospheric pressure exhaust air from the pressure intensifier is returned to the inlet to at least one of the two compressor and preferably to the inlets to both compressors to increase the efficiency of the compressors.

DETAILED DESCRIPTION OF THE INVENTION

Figure 1:
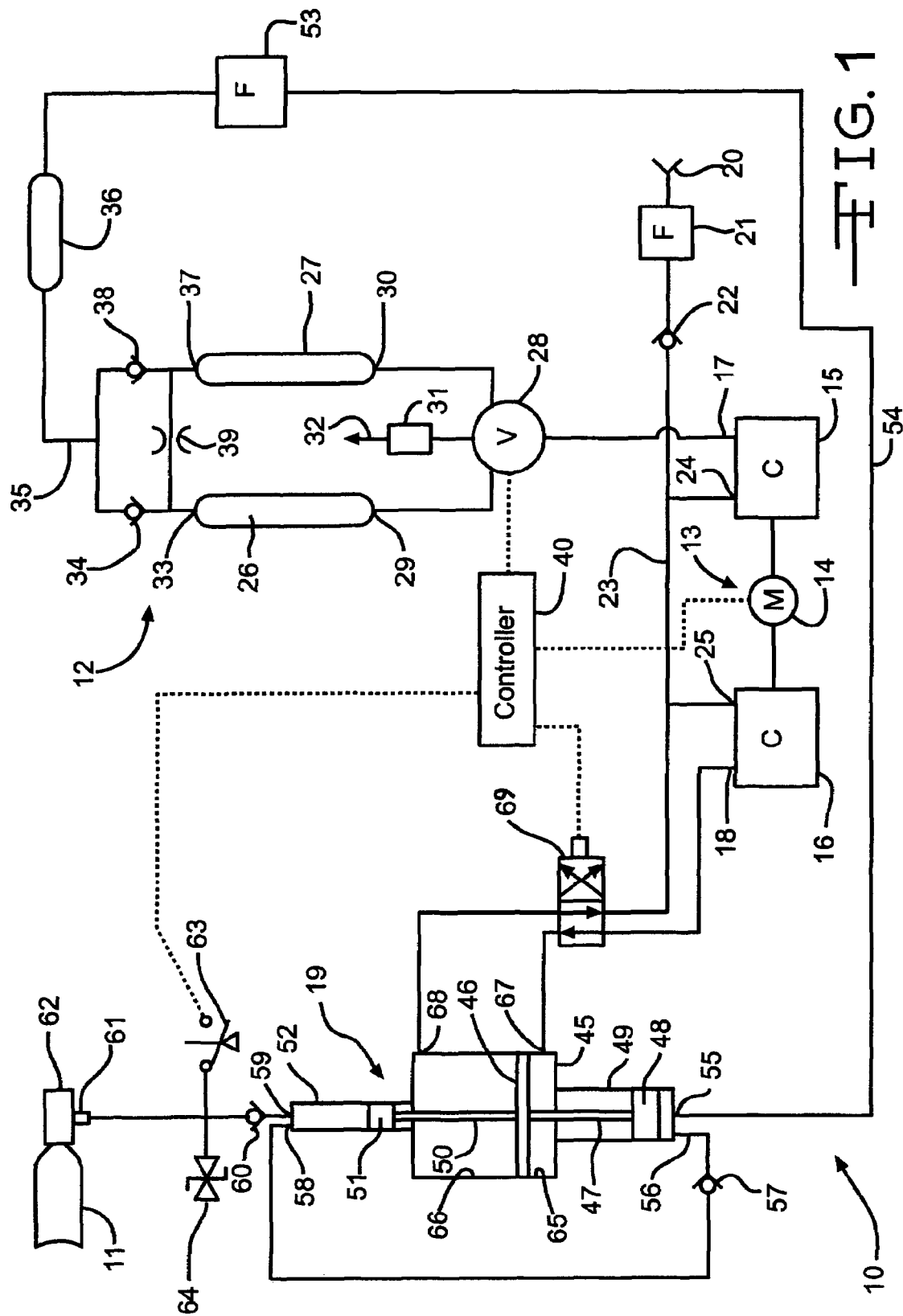
FIG. 1 is a schematic diagram of a cylinder filling oxygen concentrator according to the invention.

FIG. 1 shows apparatus 10 for filling a portable gas cylinder 11 with oxygen enriched product gas from an oxygen concentrator 12. The apparatus 10 includes a compressor unit 13 having a single motor 14 which drives two reciprocating piston compressors 15 and 16 from opposite ends of a motor shaft in a manner well known in the art. Each compressor 15 and 16 has a piston (not shown) mounted to reciprocate in a cylinder (not shown), an inlet port and an outlet port. For a conventional compressor unit of this type, the inlet ports for the two compressors 15 and 16 may be connected together and the outlet ports for the two compressors 15 and 16 are connected together. Alternately, the outlet port from one compressor 15 or 16 may be connected to the inlet port of the other compressor 16 or 15 to provide a higher outlet pressure at a lower flow rate. According to one aspect of the invention, the outlet ports for the two compressors 15 and 16 are not connected together. An outlet port 17 from the compressor 15 provides pressurized air for operating the oxygen concentrator 12, and an outlet port 18 from the compressor 16 provides pressurized air for driving a pressure intensifier 19.

An ambient air inlet 20 is connected through a filter 21 and a check valve 22 to a line 23 which is in turn connected to an inlet port 24 to the compressor 15 and to an inlet port 25 to the compressor 16. The oxygen concentrator 12 includes two molecular sieve beds 26 and 27, or other filter elements which will pass oxygen molecules while preventing the passage of nitrogen molecules. The pressurized air outlet port 17 from the compressor 15 is connected through a valve 28 to inlets 29 and 30 to the molecular sieve beds 26 and 27, respectively. The valve 28 also is connected through a muffler or noise reducer 31 to an exhaust vent 32. An outlet 33 from the molecular sieve bed 26 is connected through a check valve 34 and a line 35 to an accumulator 36 which stores oxygen enriched product gas from the oxygen concentrator 12. An outlet 37 from the molecular sieve bed 27 is connected through a check valve 38 to the line 36, also for delivering oxygen enriched product gas to the accumulator 36. The outlets 37 and 38 are also connected together through a flow restricting orifice 39.

The valve 28 is of a known type used in oxygen concentrators and may be one or more solenoid operated valves or a rotary valve, for example. In a first operating mode, the valve 28 applies pressurized air from the cylinder outlet port 17 to the inlet 29 on the molecular sieve bed 26 and connects the inlet side 30 of the molecular sieve bed 27 to the exhaust vent 32. Gas composed primarily of oxygen passes through the sieve bed 26 and the check valve 34 to the accumulator 36. A small portion of the product gas at the outlet 33 also flows through the orifice 39 and the outlet 37 of the sieve bed 27 to purge nitrogen from the sieve bed 27. In a second operating mode, the valve 28 applies pressurized feed air to the inlet 30 of the molecular sieve bed 27 and connects the inlet 29 to the sieve bed 27 to the exhaust vent 32. Oxygen rich product gas flows from the outlet 37 through the check valve 38 to the accumulator 36, and through the orifice 39 to the outlet 33 of the sieve bed 26 to purge nitrogen from the sieve bed 26. A controller 40 periodically cycles the valve 28 so that the molecular sieve beds 26 and 27 alternately operated in filter and purge modes. It will be appreciated that the oxygen concentrator 12 may have more than two gas separating elements, and that the valve 28 may have more than two modes. For example, the sieve bed 27 may be purged for only a portion of the time the sieve bed 26 is operating in the filter mode, and the bed 26 may be purged for only a portion of the time the sieve bed 27 is operating in the filter mode. The drawing only shows an exemplary oxygen concentrator. The invention may be implemented using various known types of oxygen concentrators.

The pressure intensifier 19 may be of a known type which has been used in the past for increasing the pressure of product gas from an oxygen concentrator for filling a portable oxygen cylinder. The pressure intensifier is shown as including a relatively large diameter cylinder 45 in which a piston 46 reciprocates. A connecting rod 47 connects from the center of one side of the piston 46 to a much smaller diameter piston 48 which reciprocates in a cylinder 49, and a connecting rod 50 connects from the center of an opposite side of the piston 46 to a much smaller diameter piston 51 which reciprocates in a cylinder 52. As the piston 46 is reciprocated in the cylinder 45, the smaller pistons 48 and 51 are simultaneously reciprocated in opposite directions in their respective cylinders 49 and 52. Thus, when the piston 48 is driven in a compression stroke, the piston 51 is simultaneously driven in an intake stroke, and when the piston 48 is driven in an intake stroke, the piston 51 is simultaneously driven in a compression stroke.

The oxygen enriched gas from the accumulator 36 is applied through a filter 53 and a line 54 to an inlet port 55 for the cylinder 49. An outlet port 56 from the cylinder 49 is connected through a check valve 57 to an inlet port 58 for the cylinder 52. The cylinder 52 has a high pressure gas outlet port 59 which is connected through a check valve 60, a quick connect fitting 61 on a cylinder post 62 to fill the cylinder 11 with oxygen enriched gas. A pressure switch or a pressure sensor 63 and a relief valve 64 are connected between the check valve 60 and the quick connect fitting 61. The pressure switch or sensor 63 is connected to the controller 40 for indicating when the cylinder has reached its filled pressure. The controller 40 then stops the apparatus 10.

The piston 46 divides the cylinder 45 into a first chamber 65 on the piston rod 47 side of the piston 46 and a second chamber 66 on the piston rod 50 side of the piston 46. The chamber 65 connects to a port 67 and the chamber 66 connects to a port 68. The outlet port 18 from the compressor 16 is connected through a solenoid operated valve 69 to the ports 67 when the valve 69 is unactuated and to the port 68 when the valve 69 is actuated. Cycling of the valve 69 is controlled by the controller 40. In the illustrated position of the valve 69, the outlet port 18 from the compressor 16 is connected through the valve 69 to the chamber 65 and the chamber 66 is vented to drive the pistons 46, 48 and 51 in an upward direction in the orientation shown in FIG. 1. When the valve 69 is actuated, pressurized air from the compressor 16 is delivered to the chamber 66 and the chamber 65 is vented to drive the pistons 46, 48 and 51 in a downward direction. According to the prior art, the pressurized air in the chambers 65 and 66 was vented through the valve 69 to atmosphere.

According to a feature of the invention, the valve 69, when unactuated, connects the chamber 66 to the line 23 and thence to at least one of and preferably to both of the inlet ports 17 and 25 on the compressors 15 and 16 rather than venting the chamber 66 to the atmosphere. When the valve 69 is actuated, the chamber 65 is connected through the valve 69 to the line 23. The check valve 22 prevents the above atmospheric pressure exhausted from the chambers 65 and 66 from flowing through the filter 21 and the inlet 20, while allowing atmospheric air to be drawn into the inlet ports 17 and 25 when there is insufficient pressurized air vented from the pressure intensifier 19 to meet the intake needs for the compressors 15 and 16. By applying above atmospheric pressure exhaust air from the pressure intensifier to the inlet ports 17 and 18 on the compressors 15 and 16, the energy efficiency of the compressor 13 is significantly increased.

As the piston 48 is driven in an upward direction in the cylinder 48, oxygen enriched gas from the accumulator 36 flows through the filter 53, the line 54 and the port 55 into the cylinder 49. When the pistons 48 and 51 are driven in a downward direction, the gas pressure increases in the cylinder 48 and flows through the port 56 and the check valve 57 and into the cylinder 52. Since the gas volume decreases as the pressure increases and the pistons 48 and 51 have the same length stroke, the piston 51 and cylinder 52 will have a smaller diameter than the piston 48 and cylinder 49. At the end of the downward stroke of the pistons 46, 48 and 51, the position of the valve 69 changes and the pistons are driven in an upward direction. This increases the pressure of the oxygen enriched gas in the cylinder 52 and the gas flows through the check valve 60 to the cylinder 11. When the pressure in the cylinder 11 reaches a preset maximum pressure, the pressure switch or sensor 63 causes the controller 40 to stop the motor 14 to stop operation of the oxygen concentrator 12 and the pressure intensifier 19.

It will be appreciated that various modifications and changes may be made to the above described preferred embodiment of without departing from the scope of the following claims. The invention is shown with a compressor 15 supplying pressurized air to the oxygen concentrator 12 and a separate compressor 16 supplying pressurized air to drive the pressure intensifier 19. It will be appreciated that the apparatus 10 may be provided with a single compressor connected to provide a portion of its output to operate the oxygen concentrator 12 and to provide a portion of its output to operate the pressure intensifier 19. In this situation, the pressurized exhaust air vented from the pressure intensifier 19 is supplied to the inlet port for the single compressor. It also will be appreciated that the invention is applicable to cylinder filling apparatus having other known configurations for the oxygen concentrator and/or other known configurations for the pneumatically driven pressure intensifier.

The invention claimed is:

1. Apparatus for filling a cylinder with oxygen enriched gas comprising an oxygen concentrator having an oxygen enriched gas outlet, a pressurized air driven pressure intensifier having an inlet port connected to receive low pressure oxygen enriched gas from said oxygen concentrator and to provide high pressure oxygen enriched gas for filling a cylinder, at least one compressor having at least one inlet port and at least one outlet port connected to provide pressurized air to operate said oxygen concentrator and to operate said pressure intensifier, and wherein said pressure intensifier has an above atmospheric pressure air exhaust connected to at least one of said at least one compressor inlet port.

2. Apparatus for filling a cylinder with oxygen enriched gas, as set forth in claim 1, and wherein said at least one compressor comprises a first reciprocating piston compressor having a first inlet port and a first outlet port and a second reciprocating piston compressor having a second inlet port and a second outlet port, wherein said first outlet port is contended to provide pressurized air to operate said oxygen concentrator, and wherein said second outlet port is connected to provide pressurized air to operate said pressure intensifier.

3. Apparatus for filling a cylinder with oxygen enriched gas, as set forth in claim 2, and wherein said above atmospheric pressure air pressure intensifier exhaust is connected to said first and second inlet ports.

4. Apparatus for filling a cylinder with oxygen enriched gas, as set forth in claim 3, and further including an ambient air inlet connected through a check valve to deliver ambient air to said first and second inlet ports.

5. Apparatus for filling a cylinder with oxygen enriched gas, as set forth in claim 1, and further including an ambient air inlet connected through a check valve to deliver ambient air to said at least one of said at least one compressor inlet port.

6. Apparatus for filling a cylinder with oxygen enriched gas, as set forth in claim 1, and wherein said at least one compressor comprises an electric motor having a shaft with a first end and a second end, a first compressor having a first piston driven from said first shaft end to reciprocate in a first cylinder, a first inlet port and a first outlet port and a second compressor having a second piston driven from said second shaft end to reciprocate in a second cylinder, a second inlet port and a second outlet port, wherein said first outlet port is contended to provide pressurized air to operate said oxygen concentrator, and wherein said second outlet port is connected to provide pressurized air to operate said pressure intensifier.

7. Apparatus for filling a cylinder with oxygen enriched gas, as set forth in claim 6, and wherein said above atmospheric pressure air pressure intensifier exhaust is connected to said first and second inlet ports.

8. Apparatus for filling a cylinder with oxygen enriched gas, as set forth in claim 7, and further including an ambient air inlet connected through a check valve to deliver ambient air to said first and second inlet ports.

9. A method for reducing the energy consumption of apparatus for filling a cylinder with oxygen enriched gas, comprising the steps of:
 a) providing at least one air compressor for producing at least one flow of pressurized air:
 b) providing a flow of pressurized air from said at least one air compressor to an oxygen concentrator;
 c) providing a flow of oxygen enriched gas from said oxygen concentrator to a pressure intensifier;
 d) providing a flow of pressurized air from said at least one air compressor to drive said pressure intensifier whereby the pressure of the oxygen enriched gas provided to said pressure intensifier is increased to a level suitable for filling the cylinder, said pressure intensifier exhausting above atmospheric air; and
 e) applying the above atmospheric air exhausted from said pressure intensifier to an air inlet port to said at least one air compressor.

10. A method for reducing the energy consumption of apparatus for filling a cylinder with oxygen enriched gas, as set forth in claim 9, and wherein first and second air compressors are provided for producing first and second flows of pressurized air, said first and second air compressors each having an air inlet port; wherein said first flow of pressurized air is provided to said oxygen concentrator; and wherein said second flow of pressurized air is provided to said pressure intensifier; and wherein the above atmospheric air exhausted from said pressure intensifier is applied to said air inlet ports for both of said first and second compressors.

* * * * *